United States Patent [19]

Lyman et al.

[11] 4,334,327

[45] Jun. 15, 1982

[54] URETERAL PROSTHESIS

[75] Inventors: Donald J. Lyman; Richard G. Middleton, both of Salt Lake City, Utah

[73] Assignee: University of Utah, Salt Lake City, Utah

[21] Appl. No.: 106,175

[22] Filed: Dec. 21, 1979

[51] Int. Cl.$^3$ .............................................. A61F 1/24
[52] U.S. Cl. .......................................................... 3/1
[58] Field of Search .................... 3/1, 1.4; 128/334 R, 128/335.5

[56] References Cited

U.S. PATENT DOCUMENTS

| | | | |
|---|---|---|---|
| 3,113,586 | 12/1963 | Edmark, Jr. | 3/1.5 X |
| 3,783,454 | 1/1974 | Sausse et al. | 3/1 |
| 4,011,861 | 3/1977 | Enger | 3/1 X |
| 4,225,979 | 10/1980 | Rey et al. | 3/1 |
| 4,228,550 | 10/1980 | Salkind | 3/1 |

FOREIGN PATENT DOCUMENTS 2248015  5/1975  France .................................... 3/1

OTHER PUBLICATIONS

Djurhuus et al., "Total Replacement of Ureter by a Scurasil Prosthesis in Pigs", *British Journal of Urology*, (1974), 46, 415–424.
Ulm et al., "Total Bilateral Polyvinyl Ureteral Substitutes in the Dog", *Surgery*, vol. 45, No. 2, Feb. 1959, pp. 313–320.
Fitzig et al., "Experimental Study with the Scurasil Ureteral Prosthesis", *Investigative Urology*, vol. 15, No. 3, (1977), pp. 239–241.
Tremann et al., "Long-Term Ureteral Replacement Prosthesis", *Urology*, vol. XI, No. 4, (Apr. 1978), pp. 347–351.
Kron et al., "Prothese Choledocienne en Elastomere de Silicone", *La Nouvelle Presse Medicale*, (May 1981), pp. 1933–1935.
Bergman et al., "Block Copolyurethanes in the Urinary System", *Investigative Urology*, vol. 14, No. 6, (1977), pp. 411–416.

*Primary Examiner*—Clifford D. Crowder
*Attorney, Agent, or Firm*—Thorpe, North & Western

[57] ABSTRACT

A ureter prosthesis fabricated from copolyurethane materials which are non-reactive in the urinary environment and adapted for fixation within a patient to avoid adverse migration. This ureter prosthesis can be adapted for intermediate location along a ureter or can be constructed with one-way valve means appropriate for implantation into the bladder lumen without a resulting vesico-ureteral reflux. The ureter prosthesis includes an elongate duct having a lumen whose interior surface is ultrasmooth based on microscopic inspection. An exterior cuff with terminal and intermediate sewing projections is formed around a portion of the elongate duct to enable its fixation by suturing to appropriate muscular tissue. The utility and success of this ureter prosthesis has been confirmed in multiple testing of dogs which have survived more than a year with the prosthetic ureter in place.

18 Claims, 7 Drawing Figures

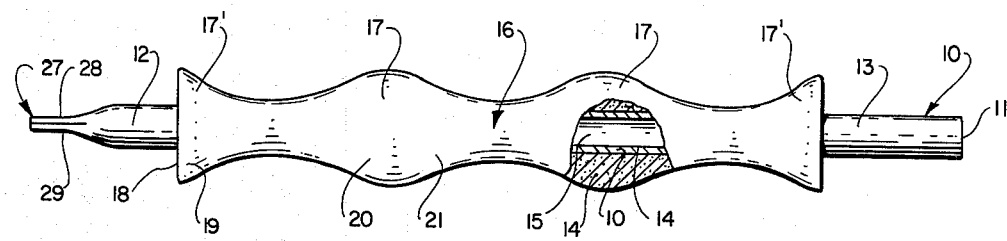
Fig. 1
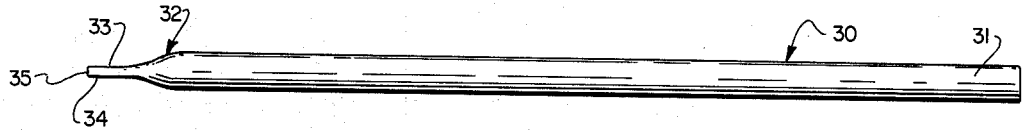
Fig. 2
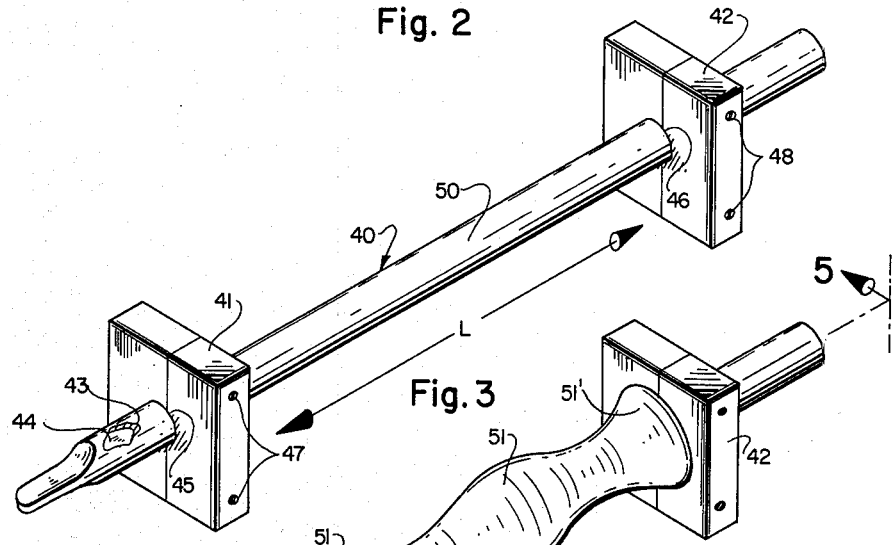
Fig. 3
Fig. 4
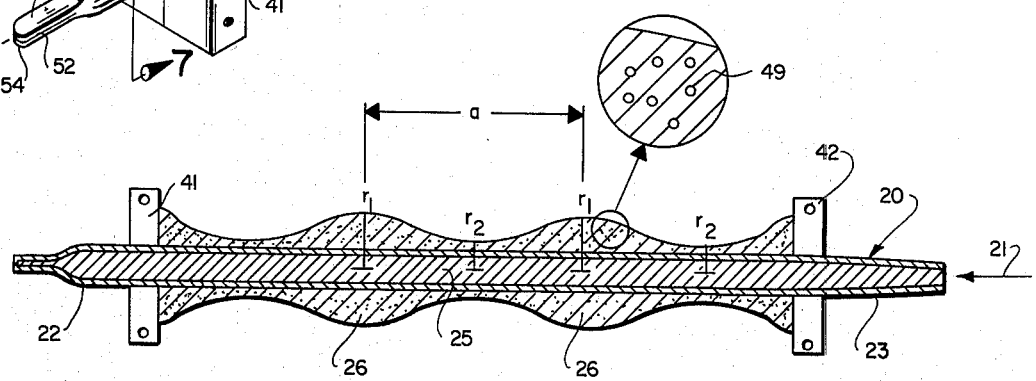
Fig. 5

URETERAL PROSTHESIS

BACKGROUND OF THE INVENTION

1. Field of the Invention

This invention relates to prosthesis devices for replacement of segments of the ureter. More particularly, it relates to a distal ureter prosthesis which is adapted to feed directly into the bladder.

2. Prior Art

The ureter is a fibromuscular tube which conveys urine from the kidney to the bladder. It begins with the pelvis of the kidney, a funnel-like dilatation and empties into the base of the bladder. A normal length for an adult ureter is approximately 16 to 18 inches.

Numerous conditions may arise which can cause the need for replacement of all or part of the ureter. Pelvic and primary carcinoma represent major causes for uretheral blockage or failure. In addition, radiation injuries, trauma and iatrogenic injuries can develop conditions requiring replacement of the ureter.

Many attempts have been made to develop a uretheral graft useful for replacing a non-terminal segment of the ureter. Experimentally in animals, segments of ureter have been replaced by abdominal wall fascia, Fallopian tubes, polyvinyl chloride, vitalium, freeze-dried arteries and veins, tantalum, polyethylene, TEFLON, and silicone rubber. The polyethylene and silicone rubber tubes have proved to be moderately successful when used to replace segments of the dog ureter.

A much more difficult challenge arises with the replacement of a distal ureter segment which empties into the bladder. Previous attempts to develop a distal ureter with a one-way valve mechanism to prevent vesico-ureteral reflux have been prepared from TEFLON, silicone rubber and stainless steel. None of these devices, however, have met with success. Common problems which have apparently led to graft failure have included migration of the implant, leakage, stenosis at the prosthesis-uretheral or prosthesis-bladder junction and incrustation with resultant hydronephrosis. Also, a general poor tolerance of the graft material has contributed to prosthesis failure in many of these cases.

OBJECTS AND SUMMARY OF THE INVENTION

It is therefore an object of the present invention to provide a ureteral prosthesis which can be successfully implanted in a human patient.

It is a further object of the present invention to provide a distal ureter prosthesis which has an acceptable life expectancy for human application.

A still further object of the present invention is to provide a ureteral prosthesis device which is not subject to failure due to incrustation or migration.

It is yet another object of this invention to provide a ureteral prosthesis device which has sufficient mechanical compliance with human tissue to prevent adverse reaction of attached tissue due to poor tolerance.

These and other objects of the present invention are realized by a novel ureter prosthesis and process of fabrication. The ureter prosthesis comprises a flexible elongate duct whose lumen has an inner diameter ranging between a normal human diameter up to as much as four times this normal human diameter size. The interior surface of the duct is ultrasmooth based on a microscopic inspection thereof. An exterior cuff is formed around a portion of the elongate duct, leaving terminal segments at each end exposed to facilitate attachment within the patient. This exterior cuff is formed of a foam-like material which has at least 40% void space therein to provide a proper density for suturing to a substantially fixed location within the patient. The ultrasmooth surface of the duct interior provides primary prevention of incrustation. The exterior cuff with its foam-like composition facilitates suturing and secure fixation of the graft not only to the ureter and bladder, but also to the psoas and retroperitoneal fascia. These features, in combination with the favorable surface characteristics and mechanical properties of the block copolymers disclosed herein provide for an operable ureter prosthesis which has proved effective in extensive animal testing.

The ureter prosthesis is adapted for distal use by coupling a one-way valve at one end of the duct to permit outflow of urine therefrom. The one-way valve prevents backflow or vesico-ureteral flux of urine. The one-way valve found most useful is a bicuspid valve which can be well adapted for the fluid pressures experienced in this segment of the urinary tract. The ureter is prepared by first selecting a tubular mandrel having a highly polished surface and an outer diameter corresponding to a desired inner diameter for the prosthesis. One end of the mandrel is configured to conform to a cavity shape which is acceptable to form the body of the valve previously referenced. The next step in this process involves applying a fluid layer of block copolymer to the mandrel. The block copolymers found particularly suitable as ureter replacement materials include copolyurethanes, copolyether-urethanes and copolyether-urethane-ureas. With the mandrel suitably coated, the copolymer layer is solidified to fix its shape in conformance with the mandrel surface. Mold blocks are then secured around terminal segments at each end of the coated mandrel to form boundaries for the formation of an exterior cuff. These blocks have an opening centrally disposed therein and corresponding to an approximate diameter of the coated mandrel to facilitate mounting the mandrel within the respective mold blocks. The cuff is formed by permanently affixing a material whose final state develops a foam-like composition over the coated mandrel between the mold blocks. Cuff thickness is selected to ensure that suturing therethrough will not intercept any of the interior material such as the duct or its lumen. Once the cuff is formed and appropriately configured to facilitate suturing to fascia within the patient, the mold blocks are removed and the mandrel is withdrawn. In addition to using the stated block copolymers as duct material, the same copolymer can be appropriately fabricated to develop the foam-like end product structure. This may be accomplished by admixing powdered inorganic salt to a solution of approximately 12 to 17% (w) block copolymer, or may utilize a fluid transfer method for establishing a 40% void throughout the cuff material.

Other aspects and features of the process and prosthesis material are outlined in greater detail hereinafter. These features, along with other objects and features of the invention will be apparent to those skilled in the art based on the following detailed description, taken in combination with the figures described and provided herein.

DETAILED DESCRIPTION OF THE DRAWINGS

FIG. 1 is a side view of a partially cut away prosthesis graft constructed in accordance with the subject invention.

FIG. 2 is a side view of a mandrel used in connection with fabrication of the subject ureter prosthesis.

FIG. 3 shows a perspective view of a partially cutaway coated mandrel with attached mold blocks.

FIG. 4 depicts a coated mandrel with attached cuff material.

FIG. 5 is a cross-section of the device shown in FIG. 4, taken along the line 5—5, including a partially exploded view of the cuff material.

DETAILED DESCRIPTION OF THE INVENTION

Figure 6:
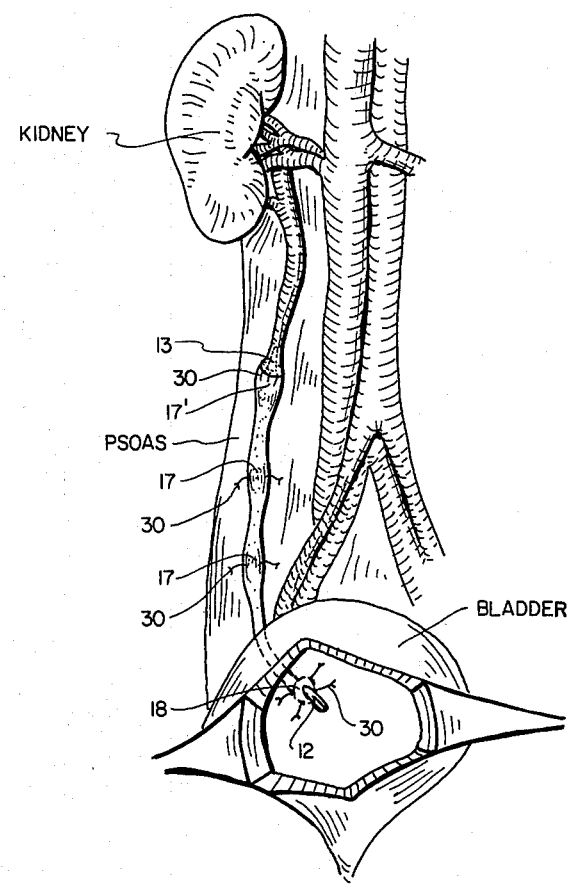
FIG. 6 shows a method for emplacement of the distal ureter graft.

Referring now to the drawings:

A distal ureter prosthesis constructed in accordance with the subject invention is illustrated in FIG. 1. The ureter comprises a substantially straight flexible, elongate duct 10 which is shown to be tubular in shape to conform to the tubular configuration of the ureter. The lumen 11 of the duct is constructed such that its inner diameter ranges from a normal ureter diameter to as much as four times the size of a normal ureter diameter as occurs in some diseased conditions. It will be apparent to those skilled in the art that the diameter size for the prosthesis device must be conformed to the ureter size of the patient which is to be treated. Furthermore, the inner diameter of the lumen may be uniform along the length of the duct 10, or it may taper from a larger diameter at a valved end 12 of the duct to a smaller diameter at the opposing duct end 13 which is secured at an open segment of the ureter of a patient. This attachment configuration with a human ureter is disclosed in FIG. 6 and discussed in greater detail hereinafter. The benefit of this tapered diameter is to prevent resistance to fluid flow as urine enters the prosthesis lumen, and continues passage therethrough to the bladder.

FIG. 5 shows a cross-section of a typical ureter prosthesis and discloses the structure of the duct 20 more clearly. As can be noted therein, the duct traverses the full length of the prosthesis beginning at an opening at one end of the lumen 21 and traversing to the valved end 22. A significant requirement of the invention is that the interior surface 16 of the duct have an ultrasmooth finish to impede incrustation within the lumen 21 of the prosthesis. As used herein, the term "ultrasmooth" refers to a material surface which appears very smooth even under microscopic examination. In other words, many surfaces which appear smooth to the unaided eye would appear very rough or textured under microscopic examination. An essential requirement of the ureter prosthesis disclosed herein is that this inner duct surface 16 must be constructed such that its surface is smooth even under microscopic examination.

The elongate duct should be flexible to permit an elastic response of the prosthesis to movement of muscular tissue to which the implant is attached. In addition, this helps prevent failure of the device due to mechanical mismatch of the prosthesis material with the body tissue to which it must conform or be compatible. Polymeric materials are particularly well suited for this application in view of their common elastic character and compatibility with body tissues. The most preferred class of polymers has been found to be a group of block copolymers represented by copolyurethanes, copolyether- urethanes, and copolyurethane-ureas. The use of these materials and their method of fabrication is discussed in greater detail hereinafter.

Circumscribing the duct 10 is an exterior cuff 16 which is formed around a central portion of the elongate duct. The purpose of the cuff is to provide an exterior material to the duct which facilitates suturing or other attachment of the prosthesis to the ureter and other tissue to which the device is attached. Although composition of the cuff material may vary, the material selected must include a foam-like character which has a sufficiently low density to permit easy suturing therethrough. The foam-like character of the illustrated prosthesis device is obtained by establishing a large number of small void spaces 14 (FIG. 1) and 49 (FIG. 5) throughout the cuff material. These void spaces may be measured in terms of density or in terms of total void space; however, the primary functional requirement is that of establishing sufficient strength in the cuff material to retain a suture therein, and sufficient low density to permit passage of a needle without unnecessary strain.

As a general guideline, the cuff material should have at least 40% void space made up of a generally uniform dispersion of small void cavities whose dimensions range from diameters of 10 microns to as much as 200 microns in size. Where the cavity sizes are smaller than 10 microns, the material becomes difficult to suture. At the other extreme of cavity sizes in excess of 200 microns, the material lacks strength to hold a suture, which tends to tear away from the cuff and from its fixed location within the patient. A preferred range which balances the cuff material properties between these opposing extremes is developed where the majority of void spaces or cavities have diameters within the range of 80 to 120 microns, and where the total void space over a uniform dispersion of voids within the material is at least 40%.

To further facilitate ease in securing the prosthesis device within the patient, the exterior cuff is configured with sewing projections 17, 17', 51, 51", which project outward from the duct to provide sufficient material for receiving a suture without risk of intercepting the duct or lumen thereof. As shown in the figures, these sewing projections are located along the length of the ureter prosthesis. Each sewing projection includes two opposing faces 18 and 19, 20 and 21 (FIG. 1) which operate as suture entry and exit sites. Practically speaking, the opposing faces may be opposite sides of a hump where the sewing projection is located intermediate of the two end sewing projections of the cuff. These sewing projections 17' at the cuff ends have one face 18 which is substantially flat, while the other face 19 tapers down to the normal cuff diameter.

The difference between the respective terminal and intermediate locations for the sewing projections 17" and 17 reflects their sutured location within the patient. As seen in FIG. 6 the blocked ends 17' of the cuff facilitate suturing the prosthesis in line between the ureter and the bladder. The distal face 18 of the cuff is sutured directly against the bladder, with the valved end of the duct 12 projecting into the bladder interior. The sewing projections 17 and 17' therefore provide large segments of cuff material which can be used to anchor sutures 30 without great concern for inadvertently intercepting the duct.

The prevention of such inadvertent interception of the duct lumen is extremely significant. If a suture were to pierce even a small point of the lumen surface, the ultrasmooth character thereof would be interrupted. The consequence of this perturbation over the ultrasmooth surface would be incrustation build-up beginning at that point and possibly continuing to occulude the urine flow path with consequent failure of the prosthesis device.

The radial thickness of these suturing projections 17 and 17' should be sufficiently great to allow the suture to penetrate sufficiently deep below the cuff surface to prevent tearing of the sutures through the cuff material. Such tearing could be prompted by sudden muscular exertion by the patient or even by the constant peristaltic action of the ureter or attached muscle. The consequence of torn sutures is a susceptibility of the implant to migration, kinking or other dislocation. If the ureter prosthesis is not securely attached in a fixed location, the peristaltic action of the attached healthy ureter will tend to drive the prosthesis device into the bladder wall causing kinking of the duct or serious damage to the bladder fascia. The sewing projections of the cuff permit secure fixation of the prosthesis device against the psoas as shown in FIG. 6, as well as provide good suturing locations to tie the terminal sections 12 and 13 of the duct to the ureter and bladder wall respectively.

Numerous configurations can be conceived which would be suitable for use as sewing projections as contemplated by the present invention. The specific structure illustrated in the drawings depicts these sewing projections as a plurality of annular rings 17 and 17' or 51 and 51' whose extreme radius $r_1$ is substantially greater in length than the shorter radius $r_2$ which represents the radial distance to the most thin segment of cuff material intermediate between any two respective sewing projections (see FIG. 5).

It will be apparent to those skilled in the art that such sewing projections 17 and 17' could be structured of separate material from the cuff itself, such as rings or tabs which are integrally attached to the cuff. However, as is disclosed in the attached drawings, the preferred embodiment provides a continuous and integral exterior cuff which includes the sewing projections 17 and 17' as part of a single foam-like material.

The distance a between the annular sewing rings 26 (FIG. 5) may vary depending upon the number of suturing locations required along the length of the device. Experimental research with animals has shown that the placement of sewing projections or sewing rings 26 every 1 to 3 centimeters along the length of the cuff. The exact separation distance a will be a function of the size of the ureter prosthesis, as well as its projected location within the patient. Likewise, the length of the ureter prosthesis will depend upon the needs of the patient; however, typical lengths have ranged from 8 to 24 centimeters.

In addition to the duct 10 and circumscribing cuff 16 shown in FIG. 1, the embodiment therein includes a distal valve 27 which is formed in a bicuspid configuration. This bicuspid valve 27 is representative of a general one-way valve means which is coupled at the distal end of the duct to permit outflow of fluid, while preventing backflow or reflux from fluids exterior to the duct. Such a valve is essential when the prosthesis is a distal ureter prosthesis which feeds directly into the bladder as shown in FIG. 6. Without such a one-way valve, vesico-ureteral reflux would occur through the open duct end.

A significant advantage of the present invention arises with the fact that this bicuspid valve 27 can be directly formed as part of the duct body. Using the methods of this invention, it has been discovered that the block copolymers disclosed herein can develop a bicuspid valve which opens for single directional flow when fluid pressure within the duct exceeds 2 millimeters of mercury, and withstands reverse flow without the duct in fluid pressures greater than approximately 8 millimeters of mercury. This valve 27 operates similar to a normal bicuspid valve in which the opposing valve flaps 28 and 29 respond with an open or closed condition based on the fluid pressure previously mentioned. It is to be understood that other valve configurations could be implemented which meet the requirements of one-way flow at the distal end of the ureter prosthesis.

Figure 7:
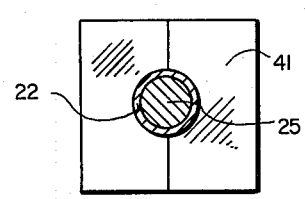
FIG. 7 is a cross section of FIG. 4 taken along lines 7—7.

In addition to a distal ureter prosthesis device, the subject invention includes an intermediate ureter prosthesis which is substantially identical with the distal ureter device, except for the absence of a valved end. Such a device is represented in FIGS. 4 and 7 as that portion of the prosthesis viewed along the line 7—7. In both the distal ureter prosthesis and the intermediate prosthesis, the terminal segments of 12 and 13 and 22 and 23 respectively, are not covered with cuff material but are left exposed for location either within the human ureter or through the bladder wall.

The implantation of this prosthesis segment would be accomplished by suturing healthy end pieces of ureter at each opposing end of the prosthesis device. Such implacement would be represented by a ureter prosthesis as shown in FIG. 6, except that rather than having the prosthesis project into the bladder, it would be coupled to the natural ureter duct which empties into the bladder void.

The characteristic features of the ureter prosthesis of the present invention can be developed by a process of manufacture which is outlined herein as part of the invention. Generally speaking, this process involves the following steps:

1. A mandrel is selected having a geometric configuration which conforms to the projected interior configuration of the prosthesis. If a intermediate ureter prosthesis is to be prepared, the end structure of the mandrel is not critical. This is because both ends of the formed prosthesis can be cut to expose the lumen of the duct formed. If, however, a distal ureter is to be formed, then one end of the mandrel should be configured to conform to a cavity shape to form the valve means required for a distal ureter prosthesis. FIG. 2 illustrates such a mandrel 30 for use in the present invention. The shape of the mandrel is tubular to match the tubular shape of a typical ureter. The mandrel diameter will serve to fix the inner diameter of the prosthesis duct in view of the formation of the duct end of the surface 31. One end of the mandrel 32 tapers from diametrically opposing sides to form two faces 33 and 34 which join at a single tapered edge 35 to form a flattened configuration which operates as a mandrel body for forming two opposing flaps which operate as a bicuspid valve.

As indicated previously, a very significant aspect of the present invention is to provide an ultrasmooth surface at the lumen interior. Therefore, the surface of the mandrel 31 must likewise be ultrasmooth based on microscopic inspection. It has been found that highly polished metals such as aluminum and stainless steel or also glass mandrels provide the desired surface to enable formation of the ultrasmooth prosthesis surface. Virtually any metal capable of being highly polished would be satisfactory, provided no adverse reaction occurs with the polymer coating.

2. A fluid layer of polymer material is then applied to the surface of the mandrel to form the duct portion of the prosthesis device. The polymers which appear to be the most effective in providing good surface characteristics compatible with blood and body tissues is a class of urethane block copolymers represented by copolyurethanes, copolyether-urethane, copolyetherurethane-ureas. The copolymer must be applied as a fluid layer to insure that the interior surface formed is ultrasmooth in character. This does not necessarily mean that the copolymer must be fluid prior to application. It simply requires the copolymer layer to be in a fluid state prior to solidification. For example, the mandrel may be wrapped with copolymer film which is then subjected to an energy source to liquify this film around the mandrel.

Another method for application is to develop a solution of copolymer and dip the mandrel into this solution to provide a smooth, even coat. Such a solution can be prepared utilizing approximately 10 to 15% (w) block copolymer in a suitable solvent. Such solvents include N,N-dimethyl formamide, N,N-dimethyl acetamide and dimethyl sulfoxide. A 15% (w) solution provides an appropriately thin coat of polymer to form the first layer of the duct body. A preferred range of viscocity for the block copolymer falls generally within a range of 0.5 to 1.0 inherent viscosity ($\eta$ inh) in N,N-dimethyl formamide at 30 degrees Centigrade. It will be apparent to those skilled in the art that other methods could be utilized to apply the block copolymer in a manner to insure that an ultrasmooth surface was developed in conformance with the highly polished surface of the mandrel.

3. The thin copolymer layer is then solidified to fix its shape in conformance with the mandrel surface. One method of solidifying the copolymer is to apply heat to enable it to dry and harden. Where the block copolymers of the suggested urethane class are used, a process of drying the material at approximately 70 degrees centigrade for 15 to 45 minutes will develop an appropriate surface structure to ensure compatibility with blood and tissue of the human body as well as preserve an ultrasmooth surface at the interior of the duct.

4. The previous steps of applying polymer material and solidifying the polymer to a thin layer fixed in shape to the mandrel surface may be repeated to develop sufficient thickness and mechanical compliance for the prosthesis duct. Generally, three to four coats are preferable; however, the actual number of coats will vary depending upon the desired thickness and strength. Although additional layers have been set forth as a specific step in this process of manufacture, it is to be understood that their use would be optional and that certain circumstances may permit the use of a single coating of polymer material to realize the benefits of this invention.

5. With the mandrel coated to a desired thickness of polymer materials, mold blocks are secured around terminal segments at each end thereof. FIG. 3 shows a coated mandrel 40 with attached mold blocks 41 and 42. The polymer coating 43 has been uniformly solidified over the highly polished surface 44 of the mandrel. The mold blocks 41 and 42 are positioned toward the end of the mandrel to block off an intermediate segment L to facilitate formation of a cuff around the coated mandrel body. These mold blocks 41 and 42 may be constructed of any suitable material (i.e. teflon) and should have openings 45 and 46 roughly corresponding to the outer diameter of the coated mandrel 40 so that the blocks can be somewhat tightly mounted thereon. The mold blocks shown in FIG. 3 are half blocks having a cylindrical indent to form the respective openings 45 and 46. Each half block is then brought from opposing sides of the mandrel to form a single cylindrical opening around the mandrel body. Screws or other fastening means 47 and 48 are used to secure the blocks to a closed configuration around the mandrel. It is to be understood that the term "mold blocks" is to be broadly contrued to mean any type of blocking means which operates to section off an intermediate portion of the quoted mandrel so that the cuff to be formed thereon is somewhat squared-off at its ends. It should be apparent, therefore, that the illustrated blocks 41 and 42 are one of many ways to accomplish this end result.

6. A cuff is then formed around the intermediate length L of the prosthesis device as illustrated in FIG. 4. This cuff is formed by permanently affixing a material whose final state develops a foam-like compositon. This foam-like composition has already been described and defined, and may be developed by numerous methods. One process which has been notably successful involves the preparation of a solution of approximately 12 to 17% (w) of the block copolymers previously referenced, followed by the admixture of sufficient powdered inorganic salts to develop at least a 40% void space within the material when it has reached its final state. As mentioned earlier, the void size should be in the range of 10 to 200 microns, and preferably in the specific range of 80 to 120 microns to properly balance strength versus suturing ease in the material. This solution is then applied to the surface 50 of the coated mandrel between the respective mold blocks 41 and 42.

The configuration of the layered material over this coated mandrel may be illustrated in FIG. 5, elements 51 and 51' which are denominated herein as intermediate sewing rings 51 and terminal sewing rings 51'. In view of the previous discussion of the function of these sewing rings, it will be apparent that other forms could be developed including another structure suitable for attachment to appropriate location within the patient. Furthermore, it will be apparent that the full length L between the mold blocks does not necessarily require the cuff coating, provided sufficient sewing projections are included to enable the device to be securely fixed in place.

With respect to the inorganic salts added to the copolymer solution, NaCl and NaHCO$_3$ are very effective for this process. In view of the requirement to have void sizes within certain ranges, the majority of salt grains should be within the range of 10 to 200 microns, and preferably between 80 and 120 microns in size. Furthermore, the total amount of salt added to the copolymer should be sufficient to develop at least a 40% void space within the cuff material as stated. Preferably, the total void space within the structure in its final product state will fall between 50 to 70%. An alternative measure of the appropriate amount of salt for the admixture of copolymer and salt powder is to provide for a ratio of salt to copolymer of 2.5:1, plus or minus 20%. In either case, the final state product is a material whose strength and suturability is appropriately balanced.

Where the cuff material is formed from the copolymer mixtures outlined previously, it may be necessary to apply additional layers of the salt copolymer admixture. The number of layers will depend upon the desired cuff thickness and type of cuff configuration selected. Each application of additional layers should be followed by an appropriate solidification step such as drying, etc.

With the cuff appropriately formed the device is allowed to stand in dionized water to accomplish the removal of salt grains and develop the final foam-like structure desired. This structure results by virtue of the fact that the salt grains are dissolved in the water solution and are thereby free to migrate out of the cuff material, leaving a somewhat uniform dispersion of void spaces corresponding to the original location of the salt grains.

A second method of realizing the foam-like structure desired for the final state of the cuff material is disclosed in U.S. Pat. No. 4,173,689. This process involves preparation of a copolyurethane composition having a molecular weight range approximately corresponding to an inherent viscosity of 0.4 to 1.0 as measured in a solution of 0.5% concentration in N,N-dimethyl formafide at 30 degrees centigrade. This copolyurethane composition is dissolved in a suitable solvent to produce a dipping solution having 5 to 12% by weight polymer concentration. This relates to a relative viscosity between the range of 100 to 1,000 at a dipping temperature of between 10 degrees centigrade to 60 degrees centigrade.

This solution is applied over at least a portion of the coated mandrel and at the exposed block faces most adjacent to the cuff location. The coated mandrel is then immersed into a precipitating solution which comprises a fluid which is miscible in the referenced solvent but operable as a precipitating non-solvent with respect to the copolyurethane composition. The coating is fixed in a stable physical structure by means of a balanced rate of exchange between the solvent and non-solvent molecules which prevents any substantial shrinkage of the coating which would otherwise destroy the void spaces fixed therein. The specific methods and procedures for such a process are thoroughly outlined in the referenced patent and are not further explicated herein.

It is to be understood that other methods of developing a foam-like material for the cuff are contemplated by the present application. In addition to the salt removal and fluid transfer methods described herein, such other methods such as foam blowing processes may be utilized to provide the desired uniform dispersion of small voids throughout the cuff material.

With the cuff formed around the intermediate section of the duct, the respective mold blocks 41 and 42 can be removed. Although not necessary, it is desirable to provide a final overall coat of block copolymer as a final protective layer over both the exterior cuff and duct. This may be accomplished by dipping this final product into a solution of 7–12% (w) of the block copolymer, followed by a subsequent drying step to solidify this final coating. The mandrel is then extracted from the prosthesis, preferably through a nonvalved end. The ends should be appropriately squared off by trimming and the final prosthesis degassed by conventional techniques. If the prosthesis formed is a distal ureter having a valved end, the valve flaps will probably require trimming along their common edge 52 as shown in FIG. 4. This can be most easily performed with the mandrel in place to provide for a clean cut to permit separation of the opposing flaps 53 and 54 in response to fluid pressures from within the duct.

EXAMPLE 1

A ureter prosthesis for distal use was fabricated by multiple solution casting of a 15% (w) solution of block copolyurethane in N,N-dimethyl formamide on a highly polished stainless steel mandrel having a shape similar to that shown in FIG. 2. The desired duct wall thickness obtained was approximately 6 to 10 mills. The coated mandrel was dried at 70 degrees centigrade for 15 minutes. Subsequent layers (ranging from 4 to 8 in total number) were cast by a similar procedure, each followed by a 15 minute drying period. TEFLON mold blocks were clamped over the coated mandrel toward each end, to leave exposed terminal segments of the coated material.

A second casting solution of similar concentration of approximately 15% (w) solids containing 2.5 parts of powdered sodium chloride per one part of polymer was layered onto the coated mandrel. Each layer was dried under similar conditions to the drying step previously applied to layers of the coated mandrel. Here again, multiple coatings of the second casting solution were applied to develop a desired thickness of the cuff and to provide annular sewing rings as shown in FIG. 4. To insure proper size for void spaces within the cuff material, a majority of the sodium chloride grains had diameters ranging between 80 to 120 microns.

After the cuff material was layered as illustrated in FIG. 4, the prosthesis was then soaked in dionized water for up to 48 hours to remove the excess sodium chloride. The prosthesis was then dried and a final coating of block copolyurethane solution having 10% solids was coated over the entire device. This coating was then dried by heating the prosthesis for 45 minutes at 70 degrees centigrade. The implant was then degassed under vacuum to remove any excess solvent.

EXAMPLE 2

Ureter prostheses having internal diameters of 2.0 millimeters and lengths of approximately 9 centimeters were fabricated in accordance with the procedure outlined in the previous example. Each prosthesis was stored in saline in a glass tube and was steam sterilized in this tube. 17 mongrel dogs weighing between 20 to 25 kilograms were anesthetized with Nembutal (20 mg./kg.) and intubated to maintain an airway. A midline abdominal incision was made, the right kidney and ureter were identified, and the distal one half or more of the ureter was excised. The free end of the ureter was sutured to the proximal end of the prosthesis with six-0 PROLENE in a continuous or running suture to form a watertight anastomosis. The short stent or exposed terminal section of the coated duct of the prosthesis facilitated this proximal anastomosis. The bladder was then opened anteriorily and a sub-mucosal tunnel was created in the right posterolateral bladder wall. The distal or valved end of the prosthesis was placed in this sub-mucosal tunnel, with the one-way valve projecting into the bladder lumen.

The sewing ring at the base of the one-way valve was fixed to the bladder mucosa and underlying muscularis with interrupted sutures of DEXON. A "psoashitch"

was performed to fix the posterolateral aspect of the bladder to the psoas facia and muscle (see FIG. 6).

After free flow of urine through the prosthesis and the one-way valve had been demonstrated, the bladder was closed with absorbable suture material. The abdominal wall was then closed. The animal was allowed to eat and drink as tolerated postoperatively. No antibiotics were used. Intravenous pyelography (IVP) was performed at regular intervals after the insertion of the uretheral prosthesis. At intervals, the animals were sacrificed and histologic examination and electron microscopy studies were made of the kidney, ureter, prosthesis and bladder.

Technical errors in surgery procedures in one animal led to its intraoperative sacrifice. An IVP was performed on each of the remaining 16 dogs at one month, three months, six months and one year postoperative intervals. At one month all 16 dogs were alive. Ten of these had normal intravenous plyograms without signs of hydronephrosis. Such a remarkable evidence of success was more than expected and highly gratifying, particularly where previous methods had always resulted in a more serious state of hydronephrosis. Four dogs exhibited minimal hydronephrosis with no delay in the appearance of contrast in the ureter. The remaining 2 dogs developed moderate hydronephrosis with delayed appearance of contrast in the ureter.

During the interval from 1 to 3 months, 2 dogs were inadvertently removed from the vivarium. Both of these dogs had shown normal IVP's at the one month interval. Of the remaining 14 dogs, 11 were still normal at the 3 month IVP. Of the 3 remaining dogs, one had an unchanged condition from the moderate hydronephrosis previously detected. Another of these dogs had shown some improvement from its previous IVP and the remaining dog developed moderate hydronephrosis from its previous normal state. One of these dogs died from an anesthesia complication after the 3 month IVP; however, its autopsy revealed no problems with the ureter implant.

During the remaining months of the test period, selected animals were sacrificed to determine the extent of possible migration of the prosthesis, as well as microscopic analysis of the affected organs and prosthesis device. Virtually all of these results confirmed the utility of the implant constructed in accordance with this invention. At this time, 5 dogs remain alive with functional uretheral prostheses even after one year following implantation. The primary remaining problem is the prevention of pyelonephritis or anastomatic disruption caused by infection. Since such infections are capable of control by antibotics, the subject copolyurethane ureter prostheses should function very well for extended periods of time.

Although preferred forms of this invention have been disclosed herein, it is to be understood that this disclosure is by way of example only and that numerous variations are possible without necessitating a departure from the scope of the invention claimed herein.

We claim:

1. A distal ureter prosthesis comprising:
   a. a substantially straight, flexible, elongate duct formed of block copolymers and having a lumen with an inner diameter approximately ranging from a normal human ureter diameter to as much as four times this size as seen in some diseased conditions, and an interior surface of said block copolymer which is ultrasmooth based on microscopic inspection;
   b. one-way valve means coupled at one end of said duct for permitting outflow of fluid therefrom, while preventing backflow from fluids exterior to the duct;
   c. terminal sewing projections formed around the ends of the duct except for exposed terminal segments of the duct which project beyond the terminal sewing projections; and
   d. at least one sewing projection integrally attached to said duct at an intermediate location between the terminal sewing projections and including a site for suturing to provide means for secure fixation of the prosthesis within the patient.

2. A prosthesis as defined in claim 1, wherein the duct comprises multiple thin layers of the block copolymer integrally connected to form a single wall structure for the duct.

3. A prosthesis as defined in claim 1, wherein said sewing projections comprise multiple layers of foam-like material coupled together to form a circumscribing wall around the duct.

4. A prosthesis as defined in claim 3, wherein total void space within the foam-like material is within the approximate range of 40% to 80%.

5. A prosthesis as defined in claim 3, wherein void space in the foam-like material is made up of many small void spaces having diameter sizes within the approximate range of 10 to 200 microns.

6. A prosthesis as defined in claim 5, wherein said small void spaces have diameters within the approximate range of 80 to 120 microns.

7. A prosthesis as defined in claim 1, wherein the sewing projections material is formed from block copolymers selected from the group consisting of copolyurethanes, copolyether-urethanes and copolyether-urethaneureas.

8. A prosthesis as defined in claim 1, wherein said terminal and intermediate sewing projections comprise a plurality of annular rings circumscribing the elongate duct and having a radius substantially greater than remaining portions of the prosthesis.

9. A prosthesis as defined in claim 8, wherein said sewing projections are formed as part of a continuous and integral exterior cuff comprised of foam-like material.

10. A prosthesis as defined in claim 9, wherein said sewing projections are positioned along the exterior cuff at separation distances of approximately 1 to 3 cm.

11. A prosthesis as defined in claim 1, wherein said one-way valve comprises a bicuspid valve which opens for single directional flow when fluid pressure within said duct exceeds 2 mm Hg, and withstands reverse flow from without the duct in fluid pressures greater than approximately 8 mm Hg.

12. A prosthesis as defined in claim 1, wherein the inner diameter of the duct lumen tapers from a larger diameter at the valved end of the duct to a smaller diameter at the opposing duct end.

13. An intermediate ureter prosthesis comprising:
   a. a substantially straight, flexible, elongate duct having a lumen with an inner diameter approximately ranging from a normal human diameter to as much as four times the size as seen in some diseased conditions, and an interior surface which is ultrasmooth based on microscopic inspection thereof;

b. terminal sewing projections formed around the ends of the duct except for exposed terminal segments of the duct which project beyond the terminal sewing projections; and c. at least one sewing projection attached to said duct at an intermediate location between the terminal sewing projections and including a site for suturing to provide means for secure fixation of the prosthesis within the patient.

14. A prosthesis as defined in claim 1 or 13, wherein said duct is comprised of a material including block copolymers selected from the group consisting of copolyurethanes, copolyether-urethanes and copolyether-urethane-ureas.

15. A prosthesis as defined in claim 1 or 13, wherein the interior face of the duct has surface characteristics and properties which are substantially identical to surface characteristics developed by forming said material on a highly polished surface of glass or metal.

16. A prosthesis as defined in claim 13, wherein said sewing projections comprise multiple layers of foam-like material coupled together to form a circumscribing wall around the duct.

17. A prosthesis as defined in claim 13, wherein the sewing projection material is formed from block copolymers selected from the group consisting of copolyurethanes, copolyether-urethanes and copolyether-urethane-ureas.

18. A prosthesis as defined in claim 13, wherein said sewing projections comprise a plurality of annular rings circumscribing the elongate duct and having a radius substantially greater than remaining portions of the prosthesis.

* * * * *